(12) United States Patent
Arkles et al.

(10) Patent No.: US 9,029,586 B2
(45) Date of Patent: May 12, 2015

(54) SILANES WITH EMBEDDED HYDROPHILICITY, DISPERSIBLE PARTICLES DERIVED THEREFROM AND RELATED METHODS

(76) Inventors: Barry C. Arkles, Dresher, PA (US); Jane C. Hollenberg, Red Hook, NY (US); Yun Mi Kim, Newtown, PA (US); Youlin Pan, Langhorne, PA (US)

( * ) Notice: Subject to any disclaimer, the term of this patent is extended or adjusted under 35 U.S.C. 154(b) by 136 days.

(21) Appl. No.: 12/470,901

(22) Filed: May 22, 2009

(65) Prior Publication Data

US 2010/0105817 A1 Apr. 29, 2010

Related U.S. Application Data

(60) Provisional application No. 61/055,806, filed on May 23, 2008.

(51) Int. Cl.
| | | |
|---|---|---|
| C07F 7/04 | (2006.01) |
| C09C 1/32 | (2006.01) |
| C07F 7/18 | (2006.01) |
| C09C 1/24 | (2006.01) |
| C09C 1/30 | (2006.01) |
| C09C 1/36 | (2006.01) |
| C09C 1/40 | (2006.01) |

(52) U.S. Cl.
CPC .............. C09C 1/32 (2013.01); *Y10T 428/2998* (2015.01); *C01P 2006/22* (2013.01); C07F 7/1836 (2013.01); C09C 1/24 (2013.01); C09C 1/3081 (2013.01); C09C 1/3684 (2013.01); C09C 1/405 (2013.01)

(58) Field of Classification Search
CPC ... C09C 1/3081; C07F 7/1836; C07F 7/1816; C07F 7/1812
USPC .......................................................... 556/445
See application file for complete search history.

(56) References Cited

U.S. PATENT DOCUMENTS

| | | | |
|---|---|---|---|
| 4,061,503 | A | 12/1977 | Berger et al. |
| 4,151,154 | A | 4/1979 | Berger |
| 4,169,912 | A | 10/1979 | Schönafinger et al. |
| 4,344,799 | A | 8/1982 | Köhler et al. |
| 4,421,747 | A | 12/1983 | Ghyczy et al. |
| 4,567,266 | A | 1/1986 | Schaus |

(Continued)

FOREIGN PATENT DOCUMENTS

WO 2007/059842 * 5/2007

OTHER PUBLICATIONS

Abstract "The role of polarity in the structure of silanes emplyed in surface modification", (Proceedings of the International Symposium on Silanes and Other Coupling Agents), Barry Arkles et al., Jun. 2007.*

*Primary Examiner* — Margaret Moore
(74) *Attorney, Agent, or Firm* — Flaster/Greenberg, P.C.

(57) ABSTRACT

The invention provides a silane compound that includes a hydrophobic group and a silane ester group linked by a hydrophilic group for use as a surface treatment to an inorganic material, such as a pigment, the silane including a hydrophobic group and a silane ester group linked by a hydrophilic group. The invention includes a coated particle including an inorganic material coated with the silane compound(s) and methods of improving the wettability and/or dispersibility of an inorganic material such as a pigment, wherein the method comprises depositing the silane compounds on the surface of a pigment.

11 Claims, 11 Drawing Sheets

(56) References Cited

U.S. PATENT DOCUMENTS

| | | | |
|---|---|---|---|
| 4,927,950 A | * | 5/1990 | Hisamoto et al. ............. 556/419 |
| 4,996,343 A | * | 2/1991 | Karger et al. ................. 556/445 |
| 5,068,382 A | * | 11/1991 | Rauleder et al. ............. 556/445 |
| 5,354,832 A | * | 10/1994 | Chang et al. .................... 528/10 |
| 5,354,881 A | * | 10/1994 | Chang et al. .................. 556/419 |
| 2006/0292637 A1 | * | 12/2006 | Atanasov et al. .............. 435/7.1 |
| 2010/0215959 A1 | * | 8/2010 | Jonschker et al. ............ 428/403 |

\* cited by examiner

SILANES WITH EMBEDDED HYDROPHILICITY, DISPERSIBLE PARTICLES DERIVED THEREFROM AND RELATED METHODS

CROSS-REFERENCE TO RELATED APPLICATIONS

This application claims the benefit of priority under 35 U.S.C §119(e) to pending U.S. patent application No. 61/055,806 filed May 23, 2008, the contents of which are incorporated herein by reference.

BACKGROUND OF THE INVENTION

It is desirable for a broad range of water insoluble materials, including hydrocarbons, higher alkyl esters, natural and synthetic waxes, resins, and water in oil emulsions, particularly those associated with coatings and color cosmetics to contain dispersible particles in order to vary film strength, barrier properties, color and emollient character. The dispersion of pigments can be controlled by a number of methods including introducing surface charge (controlling zeta potential) and modifying hydrophobicity or hydrophilicity. In most of these approaches the pigment's surface is considered to present a homogeneous surface that dictates the dispersibility of the particle. A simple example is the inability to disperse pyrogenic silica as a stable suspension in water after it has been made hydrophobic by treatment with hexamethyldisilazane despite the fact that it is denser than water. In the absence of treatment, pyrogenic silica sinks in water and forms agglomerates. On the other hand, the hexamethyldisilazane silica disperses well in hydrophobic media such as silicone and mineral oils.

The use of organosilane treatments to improve the wetting and dispersion of pigments and fillers in a variety of vehicles is well known. U.S. Pat. No. 4,169,912 teaches alkyl, alkenyl, or aryl silane surface treatment of iron oxides to improve dispersibility in organic media. U.S. Pat. No. 4,344,799 discloses the use of alkyl silane treatment to produce a titanium dioxide pigment that is readily dispersible in lacquers and plastics. U.S. Pat. No. 4,421,747 discloses high solids coatings having reduced viscosities, achieved by pre-treating pigments with alkyl silanes and titanates. U.S. Pat. No. 4,578,266 teaches that use of polysiloxane coatings on pigment formed by treatment with reactive silicones or silanes permits the incorporation of unexpectedly high amounts of pigment in silicone-containing systems.

Silanes containing relatively hydrophilic polyethylene glycol (PEG) substituent groups also have been used to modify dispersion properties. U.S. Pat. Nos. 4,061,503 and 4,151,154 disclose the use of silanes containing at least one alkylene group to improve dispersion of pigments and fillers in resin or plastic. However, there remains a need in the art for materials that may further improve the wettability and/or dispersibility of inorganic materials, such as pigments.

BRIEF SUMMARY OF THE INVENTION

The invention provides a silane compound that includes a hydrophobic group and a silane ester group linked by a hydrophilic group (such that the hydrophilic group is "embedded" within or acts as a link or bridge between the hydrophobic group and the silane ester group) for use as a surface treatment to an inorganic material, such as a pigment. This silane compound is found to be effective in improving wetting and dispersion of the material compared to commonly used alkyl silanes. Particularly effective are surface treatments of pigments with the silane compounds of the invention in which an alkyl chain and silane ester group are linked by an embedded PEG group.

The invention provides a silane compound for use in a surface treatment of a pigment or other inorganic material, the silane including a hydrophobic group and a silane ester group linked by a hydrophilic group. Also provided are silane compounds for use in a surface treatment of a pigment or other inorganic material represented by the formula (I): $R^1$—$R^2$—$R^3$. $R^1$ represents a hydrophobic group, $R^2$ represents a hydrophilic group and $R^3$ represents a silane ester group. In an embodiment, $R^2$ comprises an ester linkage that links $R^2$ and $R^1$, either directly or indirectly.

In one embodiment, the silane compound has formula (II),

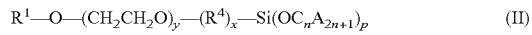

$$R^1-\!\!-O-\!\!-(CH_2CH_2O)_y-\!\!-(R^4)_x-\!\!-Si(OC_nA_{2n+1})_p \quad (II)$$

wherein $R^1$ is a hydrophobic hydrocarbon group of 6 to about 50 carbon atoms; y is an integer from 1 to about 10; x is 0 to about 10, $R^4$ is an ether linkage, an ester-containing group, a direct bond, or a substituted or unsubstituted, branched or straight chain hydrocarbon group of 1 to about 50 carbon atoms; A is independently chosen from a hydrogen atom and a hydrocarbon group of 1 to about 5 carbon atoms; n is an integer of 1 to 10 and p is an integer of 1 to 10.

The invention includes a coated particle, comprising a particle of an inorganic material having an outer surface and a coating on the outer surface of the particle, wherein the coating comprises the silane compound as noted above, wherein exemplary inorganic materials include siliceous mineral, titanium dioxide, mica, iron oxide, and ultramarine mineral pigments.

A method of improving the wettability and/or dispersibility of a inorganic material is also within the invention. The method comprises coating a surface of an inorganic material with a silane compound, wherein the silane compound comprises a hydrophobic group and a silane ester group linked by a hydrophilic group.

A composition comprising the coated particles described above are also described herein, wherein examples of such compositions may include at least one of an oil, a plastic, a thermoset polymer, a thermoplastic polymer, and a lacquer, a hydrophobic material and a material consisting of long chain esters.

The invention includes a coated particle including an inorganic material coated with the silane compound(s) and methods of improving the wettability and/or dispersibility of a pigment or siliceous particle, the method comprising depositing the silane compounds on the surface of a pigment or siliceous particle. The dispersion may be in a liquid such as a cosmetic vehicle or formulation, lacquer, a paint, or a solid such as a wax or polymer.

BRIEF DESCRIPTION OF THE DRAWINGS

The foregoing summary, as well as the following detailed description of preferred embodiments of the invention, will be better understood when read in conjunction with the appended drawings. It should be understood, that the invention is not limited to the precise arrangements and instrumentalities shown in the drawings:

FIG. 2B includes data generated by test solutions of treated red iron oxides in ethylhexylpalmitate (65% solid content);

FIG. 2C shows data generated by test solutions of treated red iron oxides in butyloctylsalicylate (60% solid content);

FIGS. 3A, 3B and 3C, show tables including viscosity data of different surface treated yellow iron oxides in various media, wherein FIG. 3A shows data generated by test solutions of treated yellow iron oxides in mineral oil (40% solid content);

FIG. 3B shows data generated by test solutions of treated yellow iron oxides in ethylhexylpalmitate (40% solid content);

FIG. 3C shows data generated by test solutions of treated yellow iron oxides in butyloctylsalicylate (40% solid content);

FIGS. 4A, 4B, and 4C show tables including viscosity data of different surface treated titanium dioxides in various media, wherein FIG. 4A shows data generated by test solutions of treated titanium dioxides in mineral oil (45% solid content);

FIG. 4B shows data generated by test solutions of treated titanium dioxides in ethylhexylpalmitate (45% solid content);

FIG. 4C shows data generated by test solutions of treated titanium dioxides in butyloctylsalicylate (45% solid content)

DETAILED DESCRIPTION OF THE INVENTION

Figure 1:
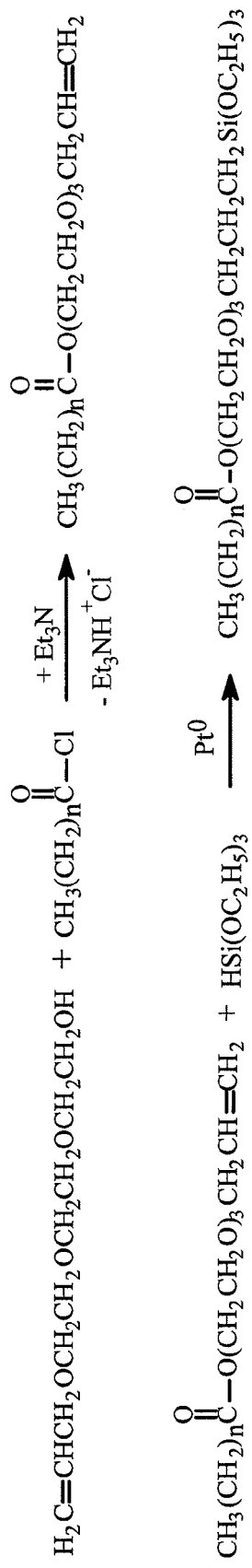
FIG. 1 shows the esterification of carboxylic acids with monoallyloxypolyethyleneoxides followed by hydrosilylation, a general method by which the silane compounds of the invention may be prepared.

The invention provides silane compounds for use in surface treatments of a pigment; particles including pigments and the silane compounds; methods of improving the wettability and/or dispersibility of a pigment; and compositions and dispersions that include the particles and/or the silanes of the invention.

Unexpectedly it has been found that wetting and/or dispersibility of pigments is improved by surface treatment with a silane that contains a hydrophobic group, and a silane ester group that are linked by a hydrophilic group (e.g., a PEG group) such that the PEG group is "embedded" within the molecule. Various new silanes with polar substitution with and without opportunities for hydrogen bonding and in which the polar groups are either embedded below a hydrocarbon tail (i.e., proximal to the surface) or tipped at the end of the hydrocarbon (i.e., polar group proximal to the contacting phase) are synthesized and analyzed herein.

In an embodiment, the silane compounds of the invention include a hydrophobic group and a silane ester group liked by a hydrophilic group. For example, the silane compound can be represented by formula (I):

In formula (I), $R^1$ is a hydrophobic group. It may be any hydrophobic group known in the art, such as for example a hydrophobic hydrocarbon group, wherein the hydrocarbon group may be an alkyl, alkoxy, alkenyl, alkynyl, aryl, alkylene ether, alkenyl ether, alkynyl ether or aryl ether group. One or more atoms of the structural backbone of $R^1$ may be independently substituted or remain unsubstituted, provided that the group preferably remains hydrophobic. The hydrocarbon group may be of any length and/or configuration (e.g., branched or unbranched) and may comprise 6 to about 50 carbon atoms, about 6 to about 20 carbon atoms, or about 6 to about 15 carbons atoms.

In an embodiment, $R^2$ of formula (I) is a hydrophilic group; any known in the art may be suitable. For example, $R^2$ may comprise at least one polyethyleneoxide group. $R^2$ may include 1 to about 10 or about 3 to about 5 polyethyleneoxide groups. Any or all atoms of $R^2$ may be independently substituted or unsubstituted, branched or unbranched. In an embodiment, $R^2$ comprises an ester linkage that links $R^1$ and $R^2$, either directly or indirectly.

The relative chain lengths of the $R^1$ and $R^2$ portions of formula (I) may be any desired. However, it may be preferred that number of atoms on the structural backbone of $R^2$ is less than the total number of atoms on the structural backbone of $R^1$. In an alternative embodiment, it may be preferred that the ratio of the number of atoms present on the structural backbones of $R^2$ and $R^1$ is about 1:2 to about 2:1 and preferably about 1:2, or, the number of atoms on the structural backbone of $R^1$ is no more than about 30% greater than the total number of atoms on the structural backbone of $R^2$. Without wishing to be bound by theory, adjusting the relative number of atoms in the structural backbones of each $R^1$ and $R^2$ in this manner may contribute to an optimization of dispersibility. For example, triethoxysilylpropoxy(triethyleneoxy)-dodecanoate-treated red iron oxide dispersed in 2-ethylhexylpalmitate demonstrated lower shear viscosity than triethoxysilylpropoxy $(PEG)_6$dodecanoate-treated iron oxide. However both had significantly lower shear viscosities than dodecyltriethoxysilane or octadecyltriethoxysilane treated controls. Similarly, compounding of triethoxysilylpropoxy(triethyleneoxy) dodecanoate-treated red iron oxide in low-density polyethylene resin demonstrated lower melt viscosity and higher tint strength, indicating better dispersion.

In a preferred embodiment, the silane compound may have formula (II),

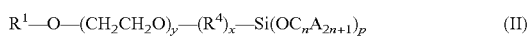

wherein $R^1$ is as discussed above; and $R^2$ is represented by $-O-(CH_2CH_2O)_y-(R^4)_x$, wherein y is from 1 to about 10, x is 0 to about 10, $R^4$ is an ether linkage, an ester-containing group, a direct bond, or a substituted or unsubstituted, branched or straight chain hydrocarbon group of 1 to about 50 carbon atoms, about 3 to about 20 carbon atoms, about 5 to about 15 carbon atoms or about 3 to about 5 carbon atoms. $R^3$ in formula (I) may be a silane-containing group, and is preferably a silane ester group as shown in Formula (II). When $R^3$ is a silane ester moiety as represented in formula (II), A is preferably independently chosen from a hydrogen atom and a hydrocarbon group of 1 to about 5 carbon atoms, and n is an integer of 1 to 10, preferably an integer of 1, 2, 3, 4, 5, or 6. In the moiety, p may be chosen from an integer of 1 to 10 or an integer of 3 to 6. In an embodiment, it is preferred that $R^3$ is capable of reacting with an oxide surface.

$R^1$, $R^2$, and $R^3$ may be attached to one another directly (by, e.g., a covalent bond) or may be joined via an intervening group or groups. For example, in an embodiment, it may be preferred that $R^2$ is joined to $R^3$ via an ester linkage or an ether linkage.

Examples of the silane compound of the invention may include triethoxysilylpropoxy(triethyleneoxy)dodecanoate, triethoxysilylpropoxy$(PEG)_6$dodecanoate, triethoxysilylpropoxy(triethyleneoxy)octadecanoate, triethoxysilylpropoxy(triethyleneoxy)dodecanoate, triethoxysilylpropoxy$(PEG)_6$octadecanoate, and triethoxysilylpropoxy$(PEG)_6$dodecanoate.

The silanes of this invention can be prepared by the esterification of carboxylic acids with monoallyloxypolyethyleneoxides followed by hydrosilylation. Any method or reaction process may be used. An example of a suitable general method is shown in FIG. 1. Other variations are possible including, but not limited to, direct esterification of the carboxylic acid rather than through the acid chloride and hydrosilylation with trichlorosilane followed by reaction with an alcohol to form the corresponding alkoxysilane.

It should be noted that by convention when referring to ethylene oxide addition products, if the adduct is named with a specific number in the nomenclature, such as triethyleneoxide, allyl ether, the chemical is nominally pure, containing exactly three ethane oxide units. If the material is denoted $PEG_3$, allyl ether, there often is polydispersity with an average of three units, but also containing 1-6 units.

The invention also includes coated particles that include an inorganic material coated with the silane compound(s) of the invention, as described above. Such particles may be prepared by coating the silane compound(s) on the inorganic material, such that the outer surface of the material has a coating including the silane compound. Such coating may be continuous or discontinuous. The coating on the silane compound may be deposited on the inorganic material, such as a pigment and/or siliceous material by any technique or method, for example, spraying, rinsing, soaking, brushing or vapor deposition. It may be preferred that the inorganic material is a pigment. Inorganic materials may include but are not limited to a siliceous minerals, titanium dioxide, mica, iron oxide, and ultramarine mineral pigments. The coatings herein are typically reactive coatings and the silane compounds react so as to create a bond with a suitable substrate. The silane compounds will preferably react in some manner in forming the coatings, either directly with the substrate as a result of a reactive moiety on the substrate such as to moisture on the substrate or the coating material will react with itself due to moisture in the system and then encapsulate the substrate. The silane esters, preferably will react with the substrate or with itself. There is typically water in the system in some form using the silane esters. In the presence of water in the substrate or from atmospheric sources, the silane esters will react with —OH on the surface of the substrate or in the presence of water the silane esters will react with itself to form a polymeric structure. If bonding to the substrate, the ester (—OR) moiety would be removed and replaced by a Si—O bond to the substrate. If there is no bonding source available on the substrate, in the presence of moisture, the ester oxidizes to form a silanol bond (Si—O) bond which will react with another such moeity and form a silsesquioxane. Therefore, one skilled in the art will understand that the coatings formed herein are typically reactive coatings, which react in some way and may or may not react so as to bond specifically to the substrate.

Methods of dispersing surface treated organic materials are disclosed herein and include methods of improving the dispersibility and/or wettability of an inorganic material, such as a pigment. The methods entail application or deposition of the silane compound described above onto an inorganic material, such as a pigment, and dispersion into a composition. The material treated with the silane compound of the invention may exhibit better dispersibility relative to silanes without embedded hydrophilic groups, silanes with homogeneous structures, or silanes with tipped hydrophilic groups Composition(s) containing the coated particles may be prepared by incorporating the coated particles into a composition. Such composition may be liquids such as cosmetic vehicles or formulations or solids such as waxes or polymer. Compositions may contain, for example, at least one of an oil, a plastic, a thermosetting polymer, a thermoplastic polymer, a lacquer, a hydrophobic material and a material having long chain esters. Examples may include oils (vegetable and mineral), petrolatum, butyloctylsalicylate, ethylhexylpalmitate, rubbers, polyolefins such as polyethylene and polyethylene, epoxy resins, urea-formaldehyde resins, phenol-formaldehyde resins, polyimides, melamine resins, acrylics, acetates, fluoroplastics, polyketones, polyesters, and celluloids. Preferably, the particles are substantially uniformly dispersed throughout the composition.

The invention is illustrated by the non-limiting examples provided below. As would have been appreciated to a person of skill in the art, in the descriptions of the examples and the technologies herein, use of the term "EO" is intended to specify the number of embedded ethylene oxide (EO) units within the silane. For example, if three EO units are embedded, the compound is referred to as "triethyleneoxide". If there is a distribution of EO units formed by polymerizing EO onto a hydroxyl group, the compound is referred to as a polyethyleneoxy (PEG) compound.

EXAMPLE 1

Preparation of
Triethoxysilylpropyltriethyleneoxydodecanoate

A 1L 4 neck flask equipped with cooling bath, magnetic stirrer, pot thermometer, addition funnel and nitrogen protected dry-ice condenser was charged with 131.3 g of lauroyl chloride, 15.0 g of triethylamine and 800 g of methylene chloride. The mixture was cooled to 5° C. Triethyleneoxide-monoallyl ether (114.1 g) was added through an addition funnel over a period of 15 minutes to the mixture while maintaining pot temperature below 15°. The mixture was stirred for 60 minutes after the addition was completed. 300 ml of water was added to the mixture to give two layers. The aqueous top layer was discarded. The bottom organic layer was washed an additional time with 300 mls of water. The organic layer was dried over sodium sulfate, filtered, and the methylene chloride removed by heating the pot to 80° C. at atmospheric pressure and then at 5 mm Hg for 60 minutes to give 201 g of a pale yellow liquid, allyloxytriethyleneoxydodecanoate.

A 1L 4 neck flask equipped with magnetic stirrer, pot thermometer, addition funnel and nitrogen protected dry-ice condenser was charged with 100 g of allyloxytriethylenoxydodecanoate, and heated to 80° C. Approximately 15 g of triethoxysilane was added to the flask followed by 0.25 ml of 2% Pt Karstedt catalyst. A slight rise in temperature was observed indicating initiation of the hydrosilylation reaction. The triethoxysilane addition was resumed, maintaining pot temperature at 75-105° over 30 minutes, until a total of 49.3 g was added. An additional 0.25 ml of Pt catalyst was added and the mixture was heated to 90° C. for 1.5 hours and then stripped under vacuum. The mixture was cooled to room temperature to give a clear yellow liquid. The product had a specific gravity of 0.977 and a refractive index of 1.4479. IR and NMR analyses were carried out and resulted in data consistent with triethoxysilylpropyltriethylenoxydodecanoate.

EXAMPLE 2

Preparation of
Triethoxysilylpropylpolyethyleneoxydodecanoate
PEG-6

A 1L 4 neck flask equipped with cooling bath, magnetic stirrer, pot thermometer, addition funnel and nitrogen protected dry-ice condenser was charged with 109.4 g of lauroyl chloride, 12.5 g of triethylamine and 365 g of methylene chloride. The mixture was cooled to 5° C. Ethoxylated allyl alcohol (PEG$_6$) (161.2) was added through an addition funnel over a period of 15 minutes to the mixture maintaining pot temperature below 15° C. The mixture was stirred for 60 minutes after the addition was completed. 300 ml of water was added to the mixture to give two layers. The aqueous top layer was discarded. The bottom organic layer was washed an additional time with 300 mls of water. The organic layer was dried over sodium sulfate, filtered and the methylene chloride removed by heating the pot to 80° C. at atmospheric pressure and then at 5 mm Hg for 60 minutes to give 210 g of a pale yellow liquid, allyloxy(PEG)$_6$dodecanoate.

A 1L 4 neck flask equipped with magnetic stirrer, pot thermometer, addition funnel and nitrogen protected dry-ice condenser was charged with 100 g of allyloxy(PEG)$_6$dodecanoate and heated to 80° C. Approximately 25 g of triethoxysilane was added to the flask followed by 0.25 ml of 2% Pt Karstedt catalyst. A slight rise in temperature was observed indicating initiation of the hydrosilylation reaction. The triethoxysilane addition was resumed maintaining pot temperature at 75-105° over 30 minutes until a total of 68.8 g was added. An additional 0.25 ml of Pt catalyst was added and the mixture was heated to 90° C. for 1.5 hours and then stripped under vacuum. The mixture was cooled to room temperature to give a clear yellow liquid with a density of 0.976 and a refractive index of 1.4479. IR and NMR analyses were carried out and resulted in data consistent with triethoxysilylpropyl(PEG)$_6$dodecanoate.

EXAMPLE 3

Preparation of
Triethoxysilylpropyltriethyleneoxyoctadecanoate

A 1L 4 neck flask equipped with cooling bath, magnetic stirrer, pot thermometer, addition funnel and nitrogen protected dry-ice condenser was charged with 75.7 g of stearoyl chloride, 6.2 g of triethylamine and 174.2 g of methylene chloride. The mixture was cooled to 5° C. Triethyleneoxidemonoallyl ether (47.6 g) was added through an addition funnel over a period of 15 minutes to the mixture maintaining pot temperature below 15° C. The mixture was stirred for 60 minutes after the addition was completed. 300 ml of water was added to the mixture to give two layers. The aqueous top layer was discarded. The bottom organic layer was washed an additional time with 300 mls of water. The organic layer was dried over sodium sulfate, filtered and the methylene chloride removed by heating the pot to 80° C. at atmospheric pressure and then at 5 mm Hg for 60 minutes to give 74 g of a pale yellow liquid, allyloxytriethyleneoxyoctadecanoate.

A 1L 4 neck flask equipped with magnetic stirrer, pot thermometer, addition funnel and nitrogen protected dry-ice condenser was charged with 65.2 of allyloxytriethyleneoxyoctadecanoate, and heated to 80° C. Approximately 5 g of triethoxysilane was added to the flask followed by 0.25 ml of 2% Pt Karstedt catalyst. A slight rise in temperature was observed indicating initiation of the hydrosilylation reaction. The triethoxysilane addition was resumed maintaining pot temperature at 75-105° over 30 minutes until a total of 33.1 g was added. An additional 0.25 ml of Pt catalyst was added and the mixture was heated to 90° for 1.5 hours and then stripped under vacuum. The mixture was cooled to room temperature to give an amber solid, with a melting point of 35-40° C. with IR and NMR analyses were carried out and the resulting data was consistent with triethoxysilylpropyltriethyleneoxyoctadecanoate.

EXAMPLE 4

Preparation of
Triethoxysilylpropylpolyethyleneoxydodecanoate
PEG-3

A 3L 4 neck flask equipped with cooling bath, magnetic stirrer, pot thermometer, addition funnel and nitrogen protected dry-ice condenser was charged with 273.5 of lauroyl chloride, 151.8 g of triethylamine and 1656 g of methylene chloride. The mixture was cooled to 5° C. Ethoxylated allyl alcohol with an average of three ethyleneoxide units (PEG3) was obtained from KAO Specialties. A compositional distribution as analyzed by HPLC indicated: EO=1: 18%, EO=2: 24%, EO=3: 23%, EO=4: 17%, EO=5 10%, EO=6: 5%, EO=7: 2%, EO>7: balance. The ethoxylated allyl alcohol (PEG 3) (292.8 g) was added through an addition funnel over a period of 45 minutes to the mixture maintaining pot temperature below 15°. The mixture was stirred for 2 hours after the addition was completed. 1000 ml of water was added to the mixture to give two layers. The aqueous top layer is discarded. The bottom organic layer is washed an additional time with 300 mls of water. The organic layer is dried over sodium sulfate, filtered and the methylene chloride removed by heating the pot to 80° C. at atmospheric pressure and then at 5 mm Hg for 60 minutes to give 400 g of a pale yellow liquid, allyloxy(PEG)$_3$dodecanoate.

A 1L 4 neck flask equipped with magnetic stirrer, pot thermometer, addition funnel and nitrogen protected dry-ice condenser was charged with 200 g of allyloxy(PEG)$_3$dodecanoate, and heated to 80°. Approximately 25 g of triethoxysilane was added to the flask followed by 0.25 ml of 2% Pt Karstedt catalyst. A slight rise in temperature was observed indicating initiation of the hydrosilylation reaction. The triethoxysilane addition was resumed maintaining pot temperature at 75-105° over 30 minutes until a total of 82.1 g was added. An additional 0.25 ml of Pt catalyst was added and the mixture was heated to 90° for 1.5 hours and then stripped under vacuum. The mixture was cooled to room temperature to give a clear yellow liquid, density 0.9613, refractive index 1.4470 with IR and NMR consistent with triethoxysilylpropyl(PEG)$_3$dodecanoate.

EXAMPLE 5

Contact Angle Analysis

Unexpectedly it has been found that wetting and/or dispersibility of pigments is improved by surface treatment with a silane that contains a hydrophobic group, and a silane ester group that are linked by a hydrophilic group (e.g., a PEG group) such that the PEG group is "embedded" within the molecule. Various new silanes with polar substitution with and without opportunities for hydrogen bonding and in which the polar groups were either embedded below a hydrocarbon tail (i.e., proximal to the surface) or tipped at the end of the hydrocarbon (i.e., polar group proximal to the contacting phase) were synthesized and analyzed. Contact angle data was gathered for both water, hexadecane and 2-ethylhexylpalmitate for each of the synthesized silanes. Control silylated surfaces were prepared with a dodecyltriethoxysilane as the hydrophobic control and a methoxy(PEG)$_{(6-9)}$propyltrimethoxysilane as the hydrophilic control. The data is shown in Table 1 below for silanes with tipped and embedded polyethylenoxy and their contact angles:

TABLE 1

| Silanes | Contact angle | | |
|---|---|---|---|
| | Water | Hexa-decane | Ethylhexyl-palmitate |
| Hydrophobic control | | | |
| dodecyltriethoxysilane | 100 | 21 | 42 |
| hydrophilic tipped silanes | | | |
| (methoxytriethyleneoxy)trimethoxysilylundecanoate | 74 | 7 | 13 |
| methoxyethoxyundecyltrichlorosilane | 73 | 5 | 9 |
| hydrophilic embedded silanes | | | |
| triethoxysilylpropoxy(triethyleneoxy)octadecanoate | 68 | 28 | 26 |
| triethoxysilylpropoxy(triethyleneoxy)dodecanoate | 62 | 6 | 12 |
| triethoxysilylpropoxy(PEG)$_6$octadecanoate | 42 | 28 | 14 |
| triethoxysilylpropoxy(PEG)$_6$dodecanoate | 35 | 3 | 11 |
| hydrophilic control | | | |
| methoxy(PEG)$_6$propyltrimethoxysilane | 16 | 17 | |

Figure 5:
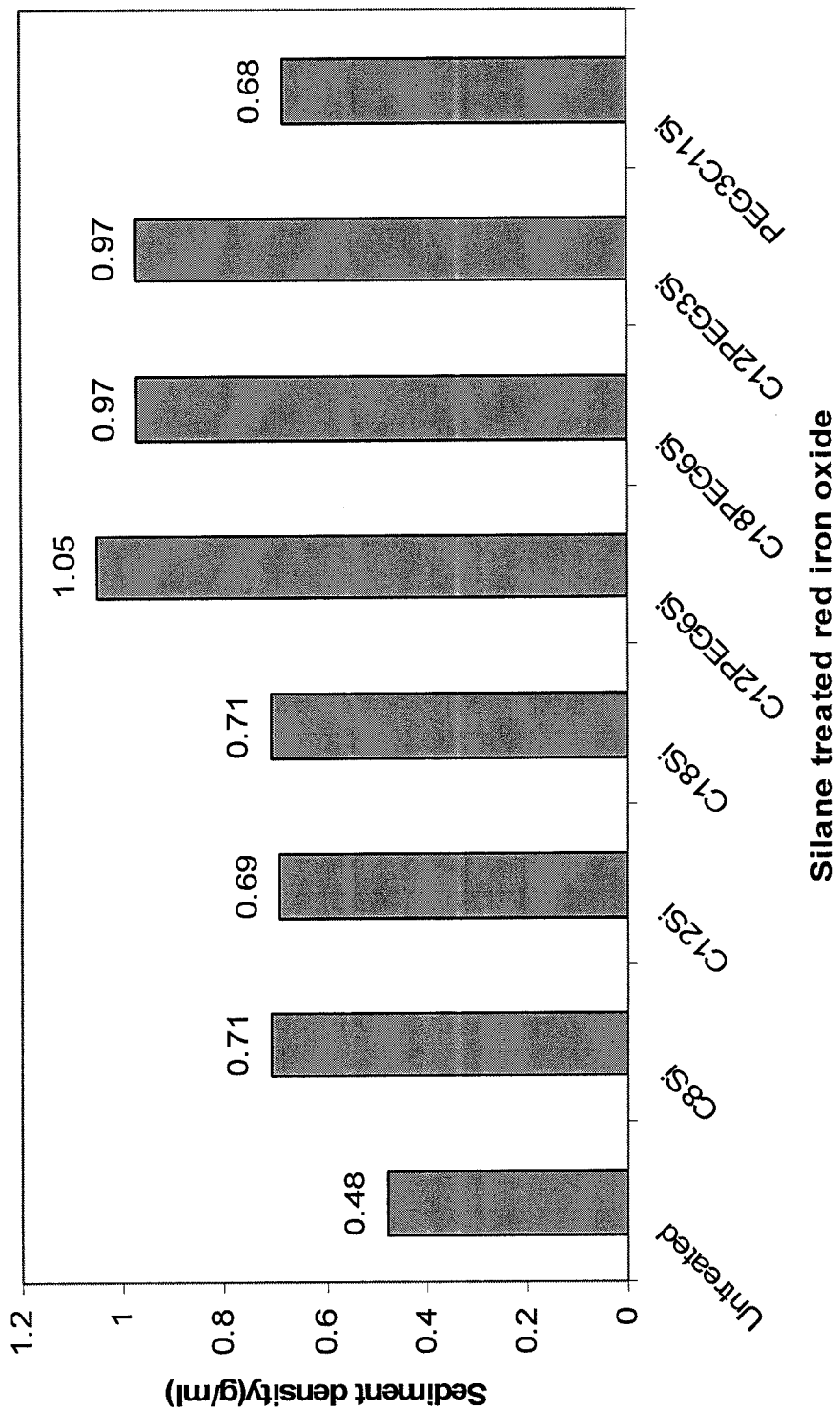
FIG. 5 shows sediment density data of silane-treated red iron oxides.

It was noted that tipped polar silanes showed higher contact angles with water than those of embedded polar silanes, regardless of opportunities for hydrogen-bonding. Further, the number of PEG units had relatively small impact on contact angle of the tipped silanes although an increase in number of PEG units correlated with decreased water contact angle. When the silanes with embedded hydrophilic groups were applied to mica and iron oxide pigments, they displayed greater dispersibility than control silanes without embedded hydrophilic groups or silanes with similar contact angles formed from silanes with homogeneous structures or silanes with tipped hydrophilic groups. The improved dispersibility was manifested by lower shear viscosity and higher sedimentation density, as shown in FIG. 5.

EXAMPLE 6

Surface Treatment Procedures on Pigments

Bulk deposition onto particulates, e.g., pigments (iron oxides, mica, TiO$_2$), fillers(clays, silica) was accomplished by a spray-on method. Sufficiently adsorbed moisture on the particles caused the hydrolysis of silanes and ultimately formed a covalent bond on the powder (Si—O-substrates). One to five wt % of the silane was prepared as a neat liquid silane. The powder was placed in a high intensity solid mixer either a twin cone mixer or a ribbon blender. The silane was sprayed onto the powder while the mixer was operated. The silane treated particles were dried and cured in trays at 80° C. for 4-8 hours. In addition to the bulk deposition method, the silane treatment can also be performed in aqueous solution or anhydrous solution, vapor deposition, and applied through the slurry treatment process.

Silanes tested were as follows: (i) triethoxysilylpropoxy(triethyleneoxy)dodecanoate (C$_{12}$PEG$_3$Si), (ii) triethoxysilylpropoxy(PEG)$_6$octadecanoate (C$_{18}$PEG$_6$Si), (iii) methoxy(PEG)$_6$propyltrimethoxysilane ((PEG)$_{(6-9)}$C$_3$Si), (iv) n-dodecyltriethoxysilane (C$_{12}$Si), (v) n-octyltriethoxysilane (C$_8$Si), and (vi) n-octadecyltrimethoxysilane (C$_{18}$Si).

The silane-treated powders, red iron oxide, yellow iron oxide, and TiO$_2$, were dispersed into mineral oil, ethylhexylpalmitate, and butyloctylsalicylate, respectively, and milled with the three-roll mill to evaluate their viscosities at a given concentration. The solvents were selected to cover a wide range of dielectric constants of the solvents, i.e., mineral oil 2.13, ethylhexylpalmitate 3.06, and butyloctylsalicylate 6.2. Untreated powder was also included in this experiment. Viscosity measurements for some samples are not shown in the graphs because their viscosity was too high to provide measurement under the given conditions.

Figure 2A:
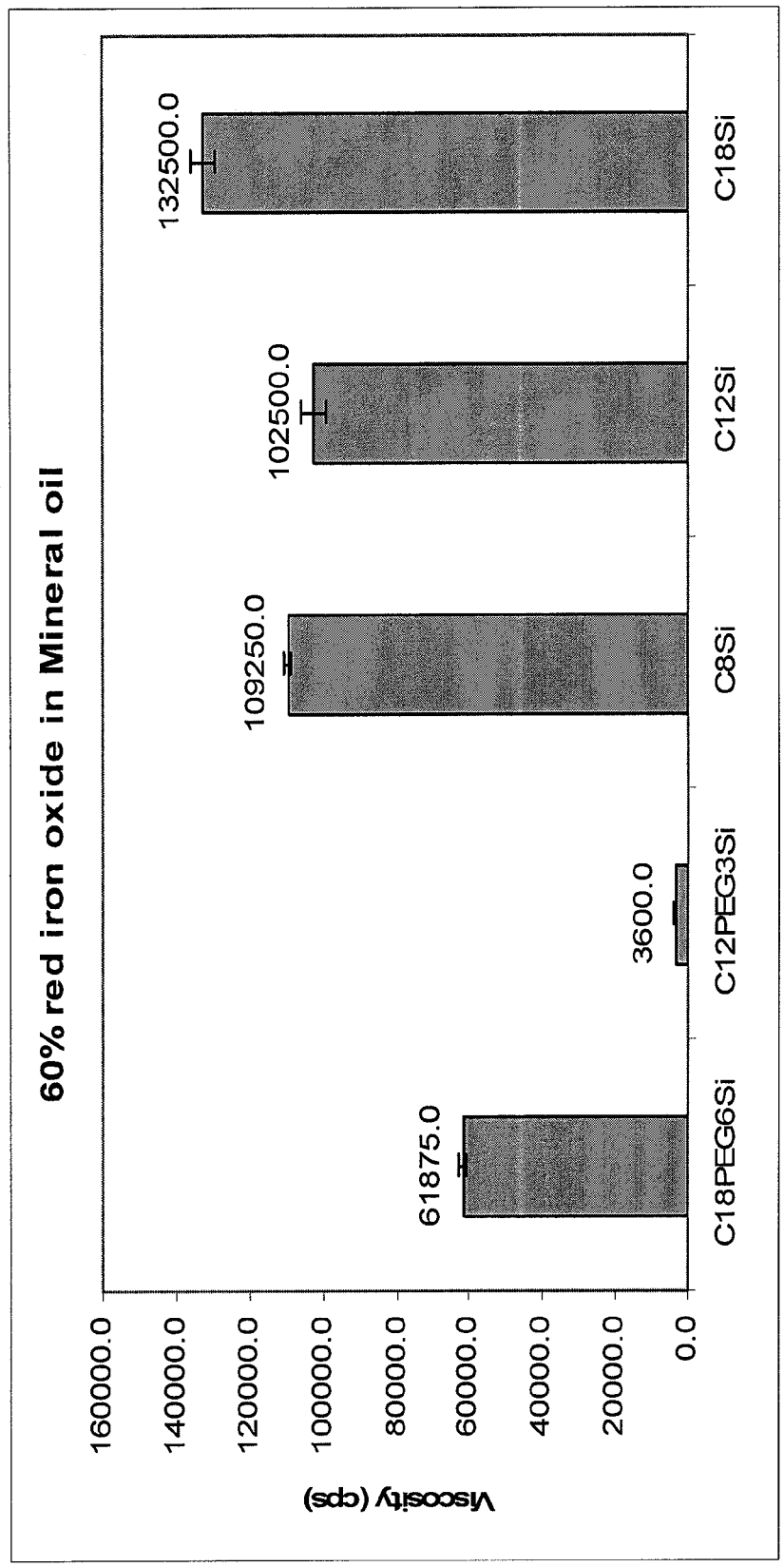
FIGS. 2A, 2B, and 2C, show tables including viscosity data of different surface treated red iron oxides in various media, wherein FIG. 2A includes data generated by test solutions of treated red iron oxides in mineral oil (60% solid content)
Figure 2B:
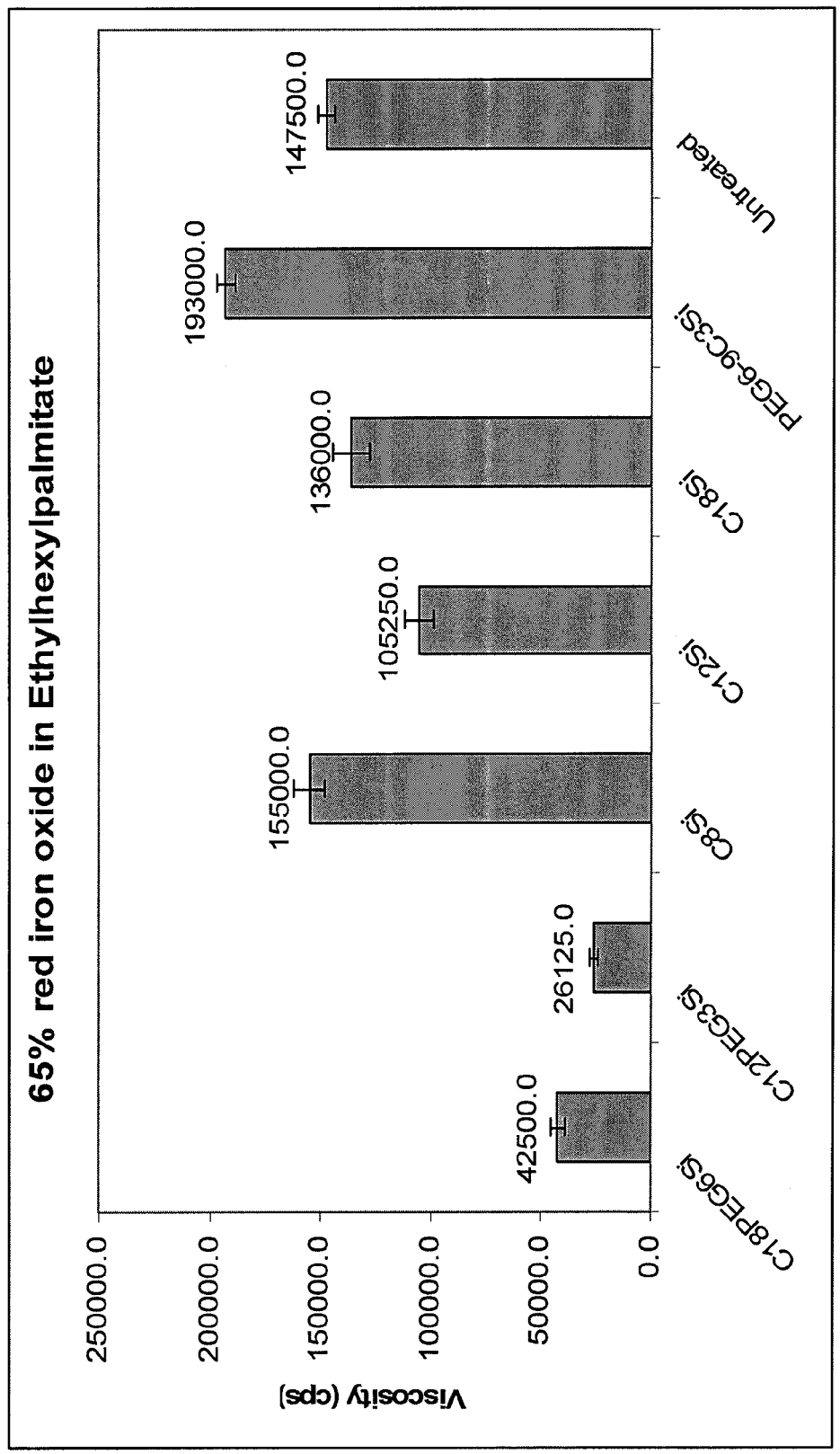
Figure 2C:
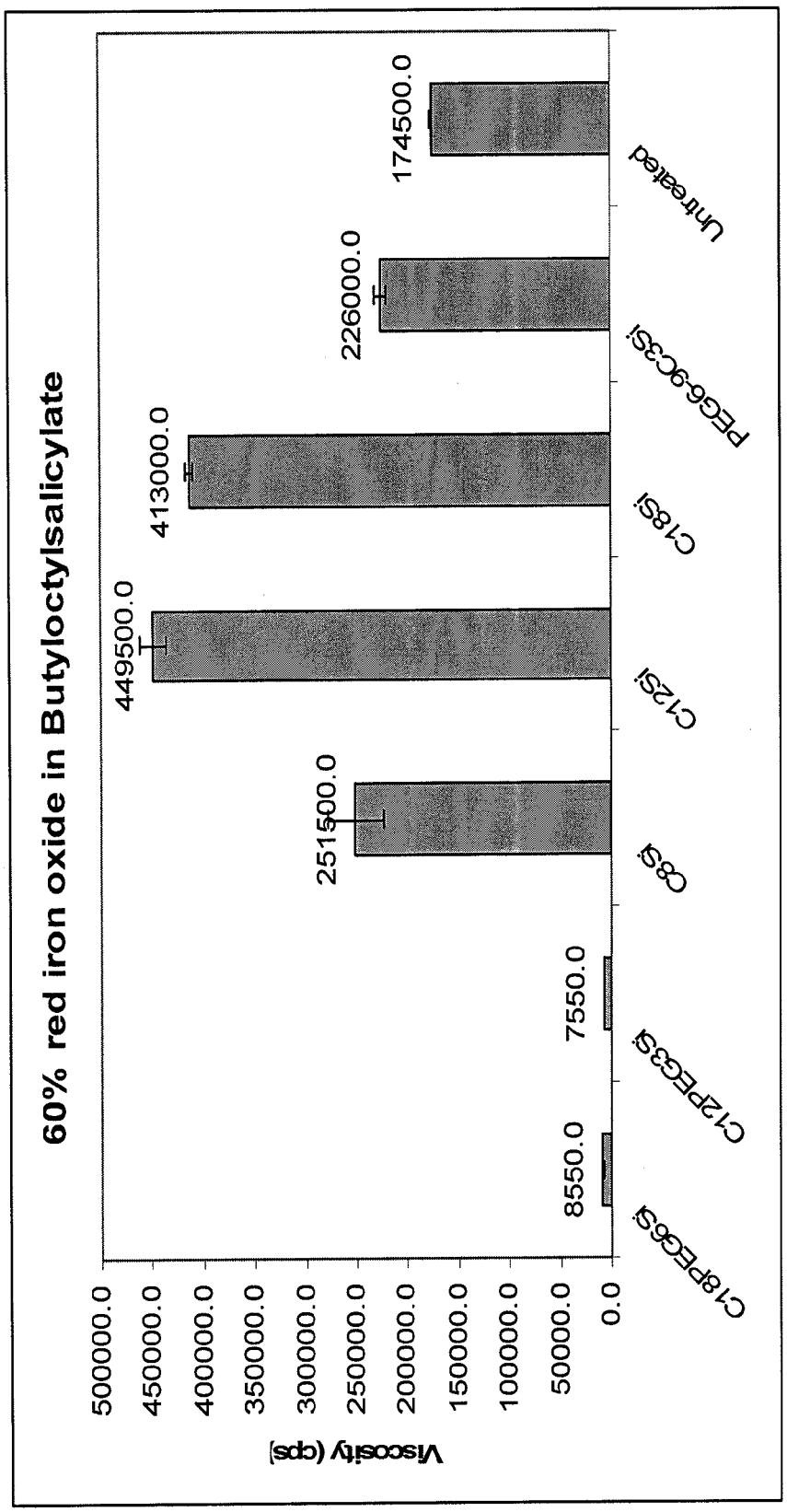
Figure 3A:
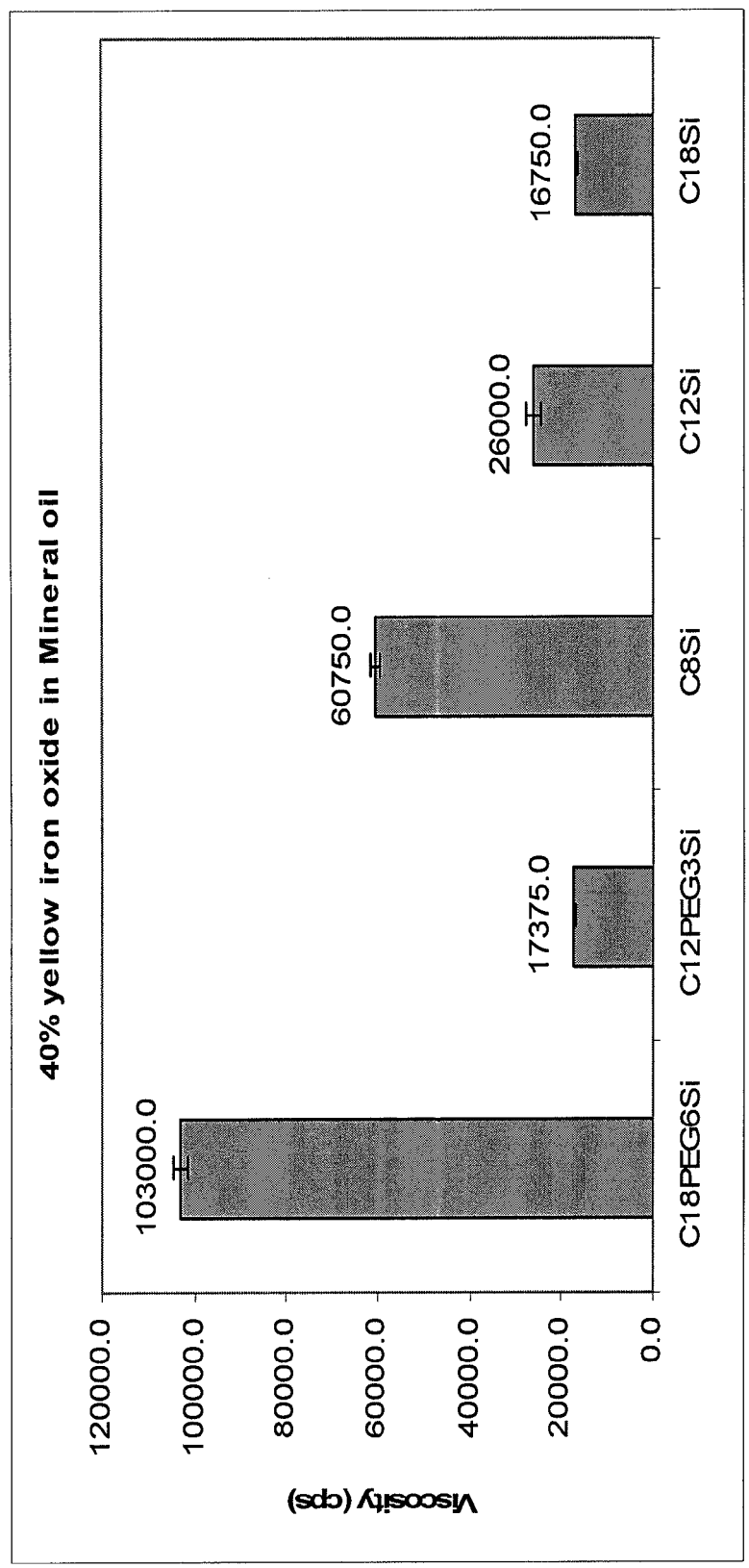
Figure 3B:
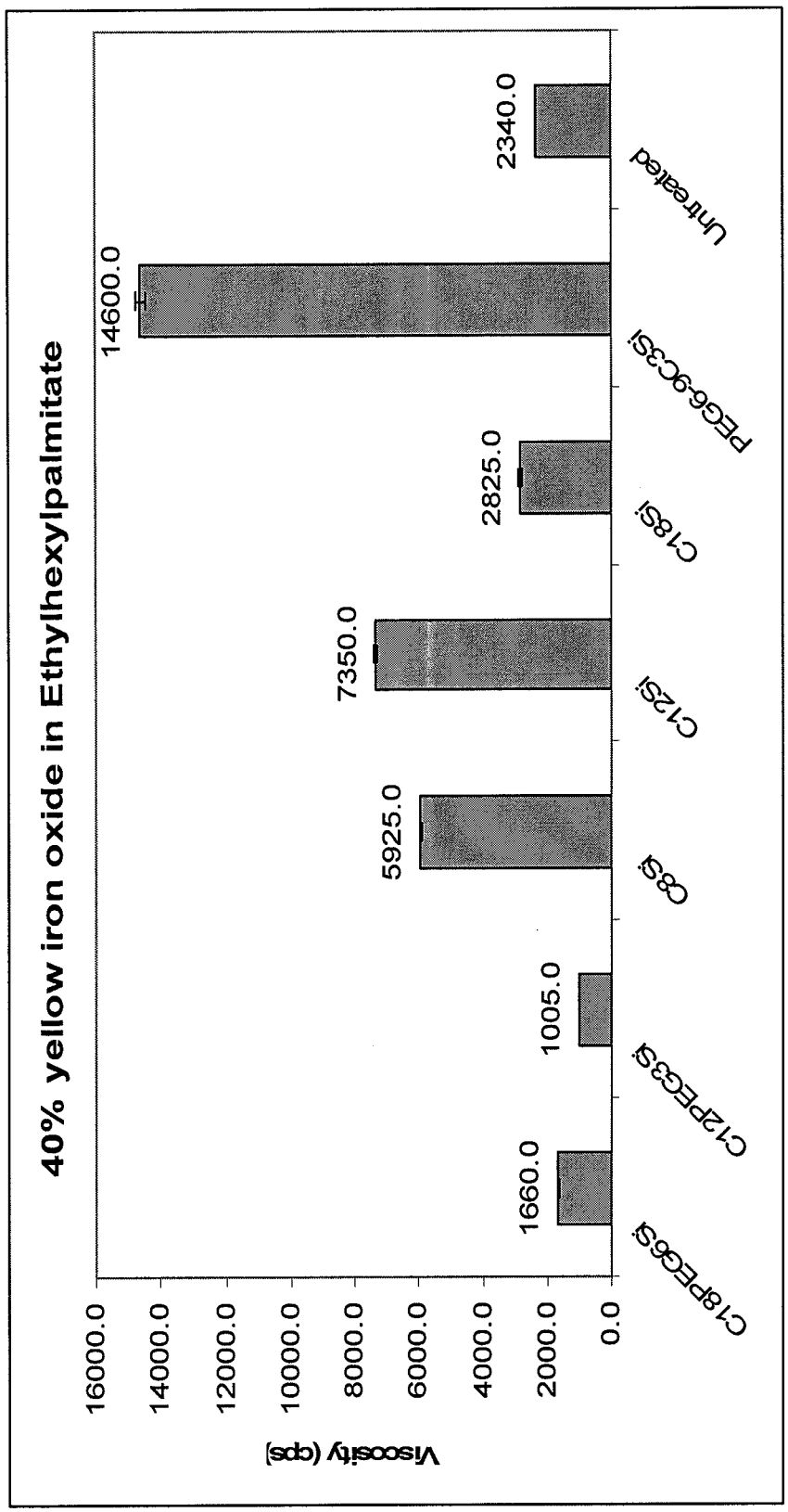
Figure 3C:
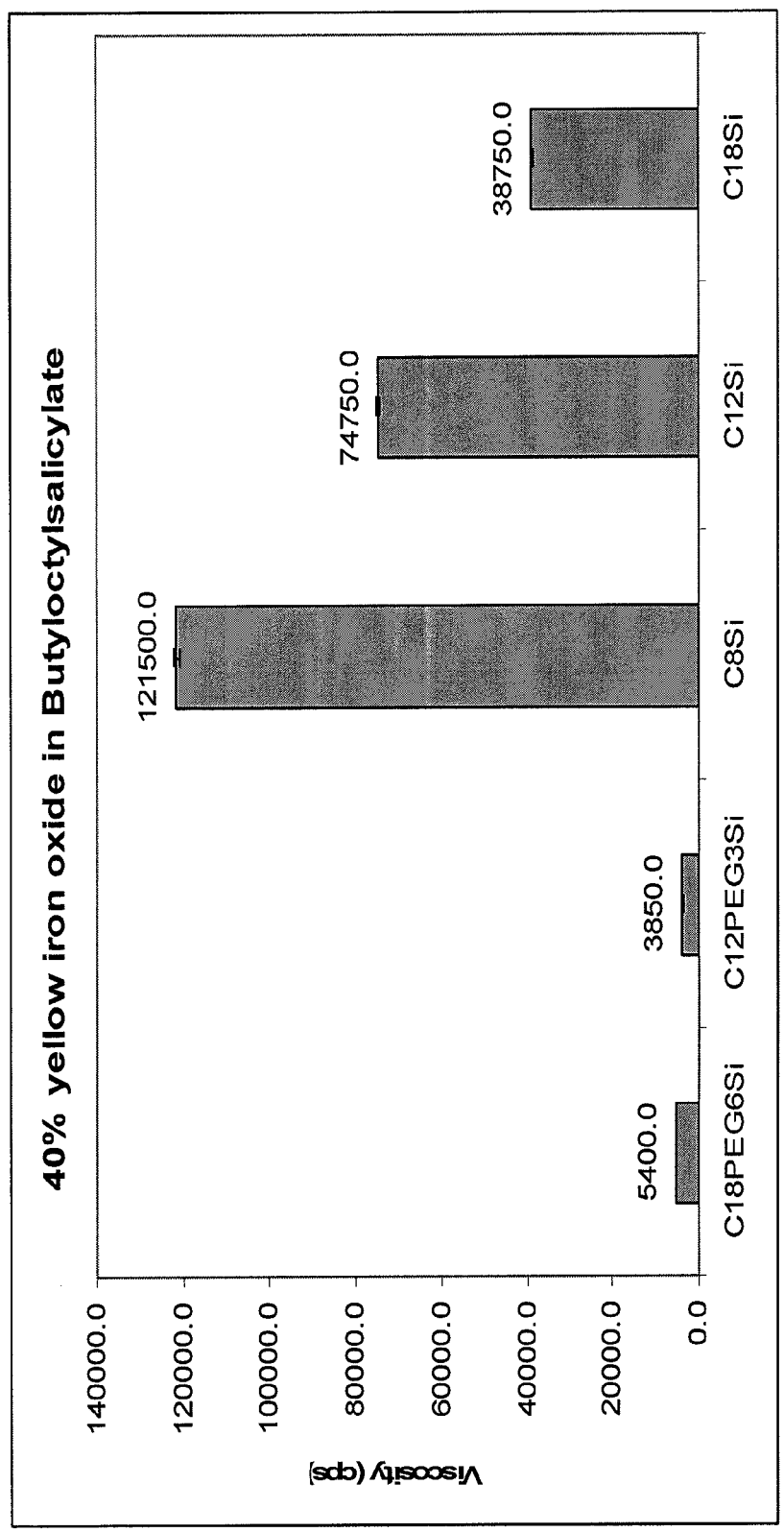
Figure 4A:
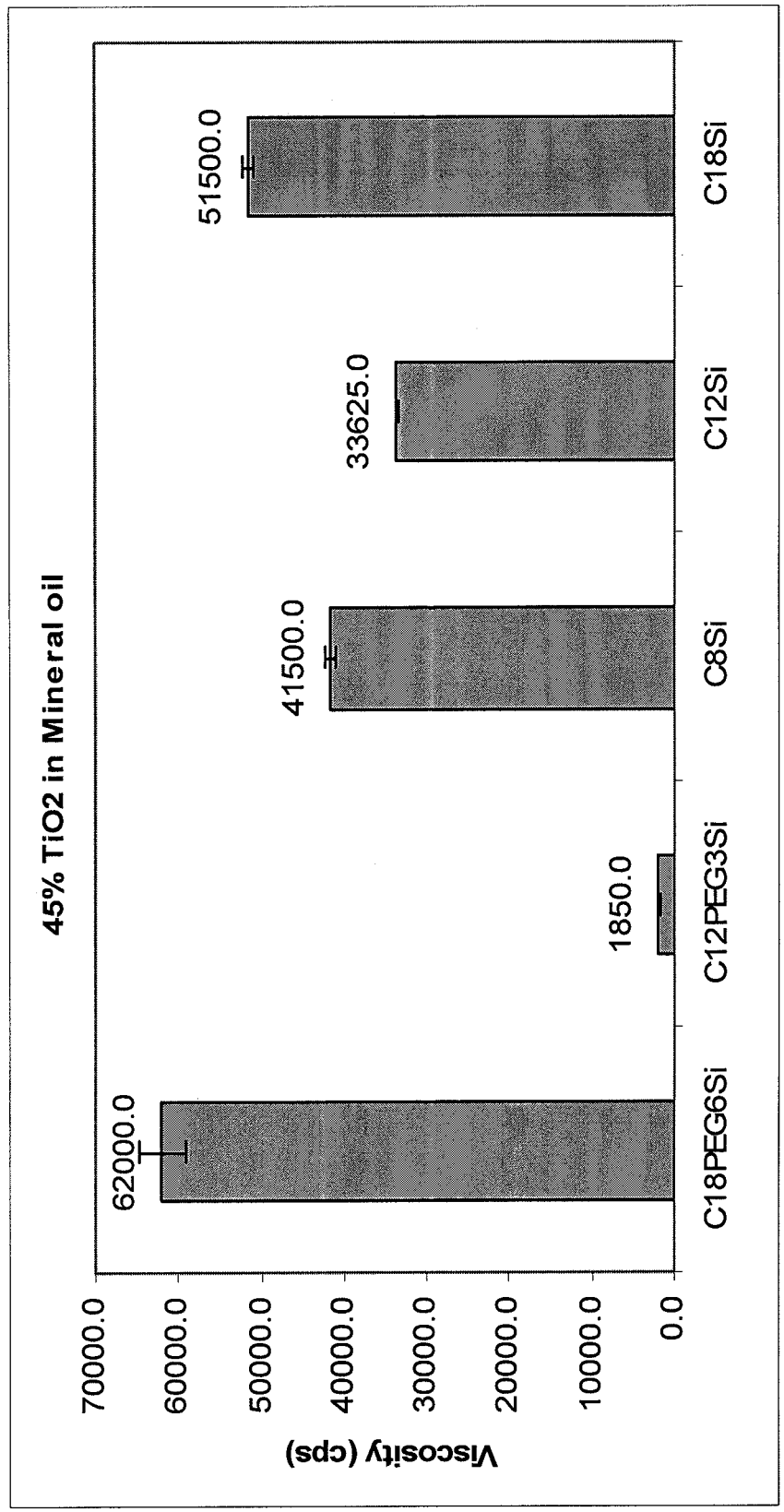
Figure 4B:
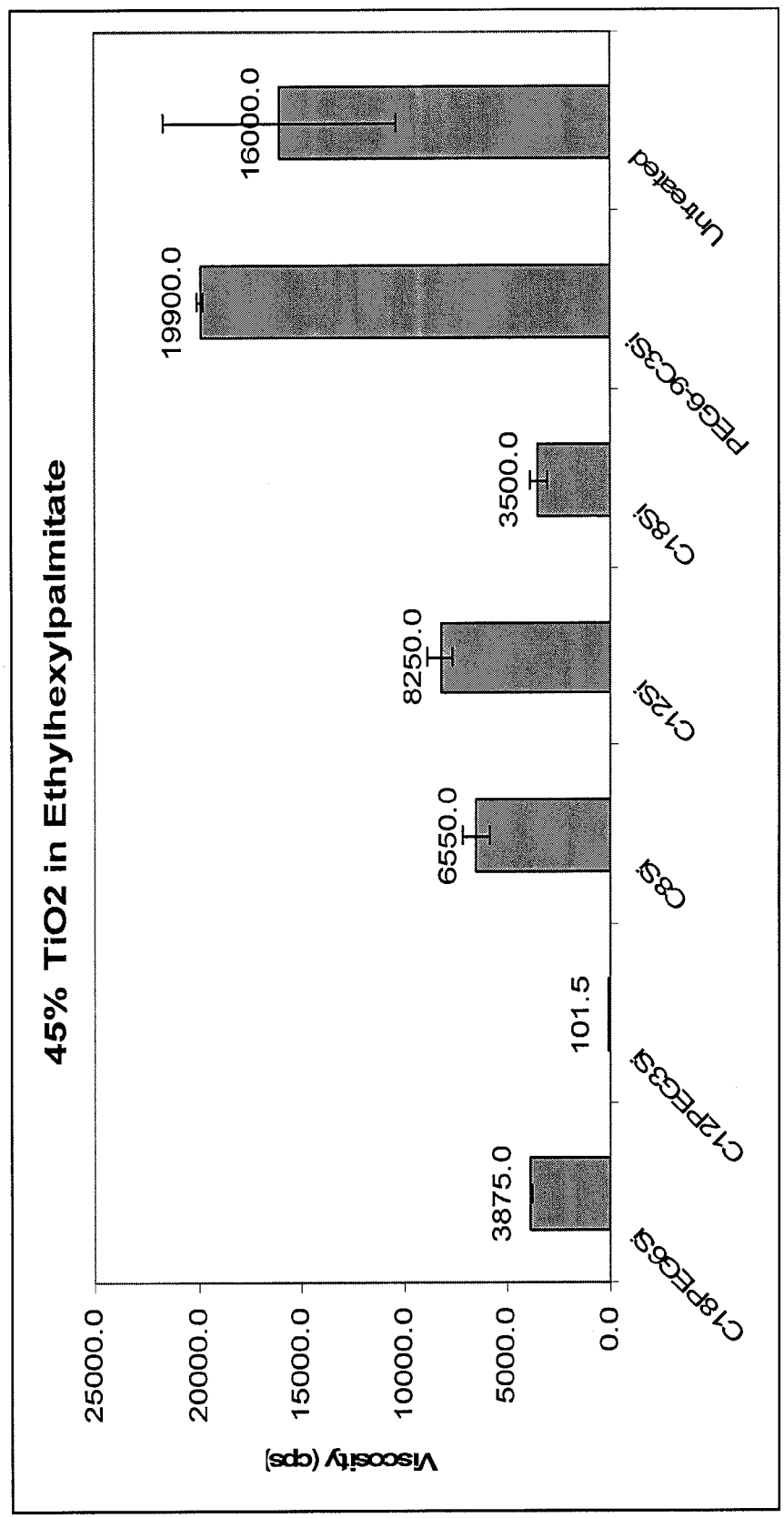
Figure 4C:
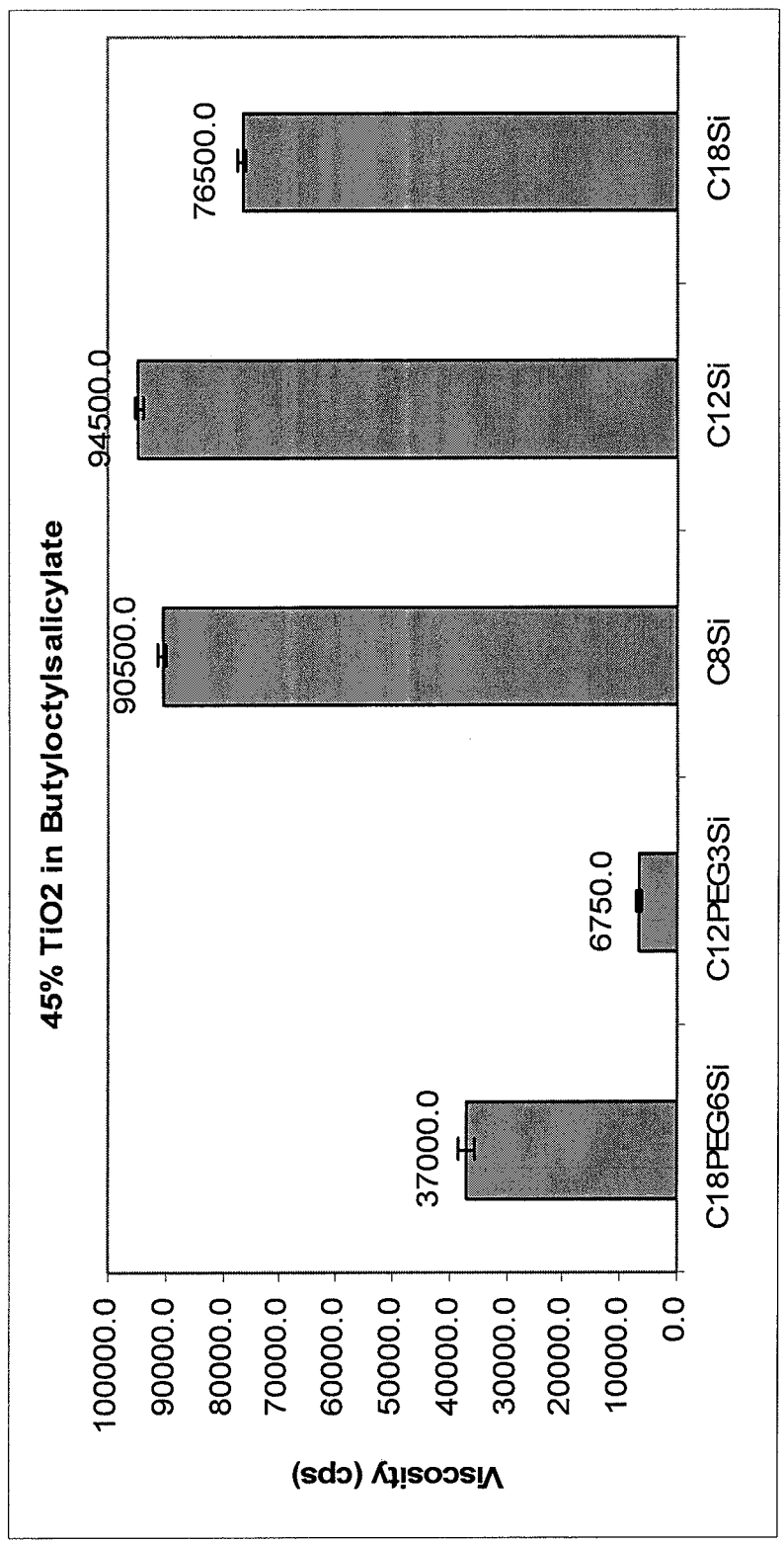

The ethyleneoxy-modified, silane-treated powders excluding the (PEG)$_{(6-9)}$Si exhibited significantly lower viscosity than those of alkylsilane treated samples, as shown in FIGS. 2, 3, and 4. The C$_{12}$(PEG)$_3$Si treatment was the most effective and steady in terms of reducing viscosity for each powder in oils. In the case of C$_{18}$(PEG)$_6$Si, its viscosity level relative to those of alkylsilanes varied with particulates and oils, suggesting that an optimum ratio of the polar to non-polar substitution on silane for good wetting may be affected by a nature of particulates and dielectric constant of the solvent.

Particulates with a poor wettability in oils tend to flocculate and lead to a greater sediment volume. In comparison, good wetting particles are deflocculated, therefore, create a higher sediment density. FIG. 5 shows that the ethyleneoxy-modified silanes have the better wetting property in ethylhexylpalmitate compared to the alkylsilanes and untreated red iron oxide. It will be appreciated by those skilled in the art that changes could be made to the embodiments described above without departing from the broad inventive concept thereof. It is understood, therefore, that this invention is not limited to the particular embodiments disclosed, but it is intended to cover modifications within the spirit and scope of the present invention as defined by the appended claims.

We claim:

1. A silane compound for use in a surface treatment of a pigment, the silane compound comprising a hydrophobic group and a silane ester group linked by a hydrophilic group, wherein the silane compound has a structure represented by formula (I):

$$R^1-R^2-R^3 \quad (I)$$

wherein R$^1$ represents the hydrophobic group and is a hydrocarbon group of 6 to about 50 carbon atoms, wherein R$^1$ links to the hydrophilic group via an ester-containing group;

wherein R$^2$ represents the hydrophilic group and R$^2$ is —(CH$_2$CH$_2$O)$_y$—(R$^4$)$_x$, wherein y is an integer from 1 to about 10; x is 0 to about 10, and R$^4$ is an ether linkage, an ester-containing group, a direct bond, or a substituted or unsubstituted, branched or straight chain hydrocarbon group of 1 to about 50 carbon atoms; and wherein the silane ester group is represented by $R^3$ and $R^3$ is —$Si(OC_nA_{2n+1})_p$; wherein A is independently chosen from a hydrogen atom and a hydrocarbon group of 1 to about 5 carbon atoms; n is an integer of 1 to 10 and p is an integer of 1 to 10.

2. The compound of claim 1, wherein the silane compound is capable of reacting with an oxide surface.

3. The silane compound of claim 1, wherein n is an integer of 2 to 6.

4. The compound of claim 1, wherein the hydrophobic hydrocarbon moiety comprises 6 to about 30 carbon atoms.

5. The compound of claim 1, wherein y in the hydrophilic group is 3 to about 9.

6. The compound of claim 1, wherein y in the hydrophilic group is about 3 to about 5.

7. The compound of claim 1, wherein the at least one polyethyleneoxide group is linked to the silane ester group via an ester linkage and/or an ether linkage.

8. The compound of claim 1, wherein a total number of atoms on a structural backbone of the hydrophilic group is less than a total number of atoms on a structural backbone of the hydrophobic group.

9. The compound of claim 8, wherein a ratio of a total number of atoms present on a structural backbone of the hydrophilic group to a total number of atoms present on a structural backbone of the hydrophobic group is about 1:2.

10. The compound of claim 1, wherein the total number of atoms on the structural backbone of the hydrophobic group is no more than 30% greater than the total number of atoms on the structural backbone of hydrophilic group.

11. A silane compound for use in a surface treatment of a pigment, the silane compound comprising a hydrophobic group and a silane ester group linked by a hydrophilic group, wherein the silane compound is selected from triethoxysilylpropoxy(triethyleneoxy)dodecanoate, triethoxysilylpropoxy(PEG)$_6$dodecanoate, triethoxysilylpropoxy(triethyleneoxy)octadecanoate, triethoxysilylpropoxy(triethyleneoxy)dodecanoate, triethoxysilylpropoxy(PEG)$_6$octadecanoate, and triethoxysilylpropoxy(PEG)$_6$dodecanoate.

\* \* \* \* \*